United States Patent [19]

Sagi

[11] Patent Number: 4,624,264
[45] Date of Patent: Nov. 25, 1986

[54] METHOD OF EARLY DETECTION OF BREAST CANCER

[75] Inventor: Zsigmond L. Sagi, Denville, N.J.

[73] Assignee: B.C.S.I. Laboratories, Inc., New York, N.Y.

[21] Appl. No.: 330,501

[22] Filed: Dec. 14, 1981

Related U.S. Application Data

[60] Division of Ser. No. 103,587, Dec. 14, 1979, abandoned, which is a continuation-in-part of Ser. No. 408,154, May 22, 1978, Pat. No. 4,190,058.

[51] Int. Cl.⁴ ............................................. A61B 10/00
[52] U.S. Cl. .................................................. 128/736
[58] Field of Search ................. 128/736; 374/162, 102

[56] References Cited

U.S. PATENT DOCUMENTS

| | | | |
|---|---|---|---|
| 3,594,126 | 7/1971 | Fergason et al. | 374/162 X |
| 3,661,142 | 5/1972 | Flam | 128/736 X |
| 3,665,770 | 5/1972 | Sagi et al. | 374/162 X |
| 3,677,088 | 7/1972 | Lang | 374/162 X |
| 3,699,813 | 10/1972 | Lamb | 128/736 |
| 3,830,224 | 8/1974 | Vanzetti et al. | 128/736 |
| 3,847,139 | 11/1974 | Flam | 128/736 |
| 3,960,138 | 6/1976 | Doss et al. | 128/736 |
| 4,030,482 | 7/1977 | Navato | 374/162 |
| 4,173,970 | 11/1979 | Momin | 128/736 |
| 4,190,058 | 2/1980 | Sagi | 128/736 |

OTHER PUBLICATIONS

Gershon-Cohen et al.; "Cancer Detection" article; Cancer; 12-1969; pp. 1226-1230.
Gershon-Cohen et al.; "Advances in Thermography and Mammography"; Annals-N.Y. Academy of Sciences; 1964, pp. 283-300.
Brueschke et al.; "Relative Densitometric Analysis of Thermograms"; Annals-N.Y. Academy of Sciences; 1964, pp. 82-89.

Primary Examiner—Kyle L. Howell
Assistant Examiner—Angela D. Sykes
Attorney, Agent, or Firm—Davis Hoxie Faithfull & Hapgood

[57] ABSTRACT

A cancer detection patch is used for aid in early detection of breast cancer by a method which involves scanning mirror image quadrants of the breast to determine the temperature thereof. The patch comprises a flexible, heat-conductive web; an array of spaced-apart temperature indicators comprising a dye, or a pigment, and a temperature-sensitive substance having a relatively precise melting point approximately 0.5° F. different from the melting point of the temperature-sensitive substance in the adjacent indicator, wherein each of said indicators displays a change in color upon melting of the temperature-sensitive substance therein; a transparent layer overlying said heat-conductive web and sealed thereto; a backing web made of a flexible, compressible material secured to the other side of the heat-conductive web and a peelable layer adhesively secured to said backing web. Mirror image quadrants of the breast are scanned by placing a patch in each of the breast-receiving cups of the brassiere, in conformable, contiguous contact with the breast skin, removing both patches after several minutes and comparing the temperature in mirror image quadrants of the breast by visual observation of the temperature indicators in each quadrant patch.

2 Claims, 5 Drawing Figures

U.S. Patent  Nov. 25, 1986  4,624,264
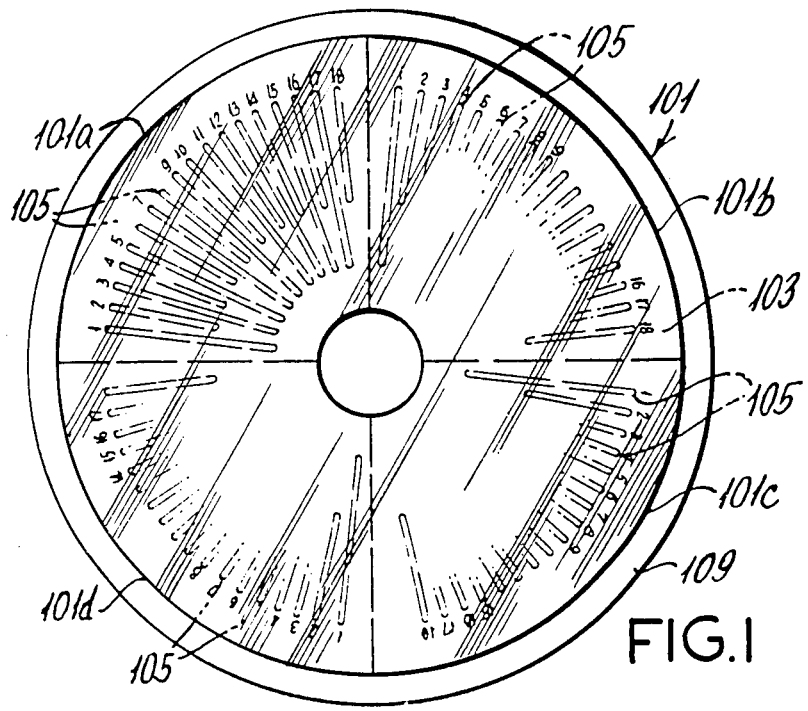
FIG.1
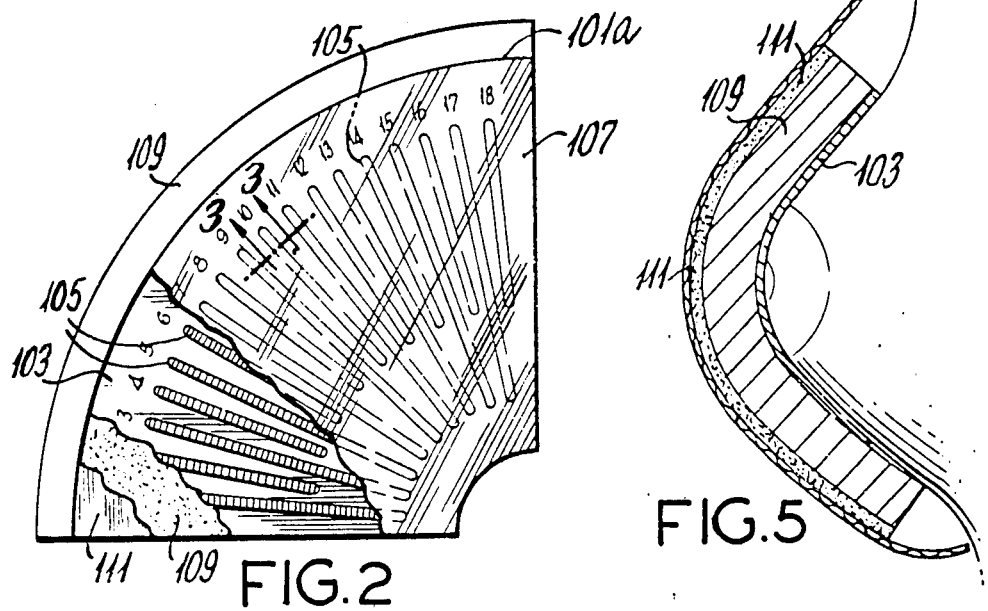
FIG.2
FIG.5
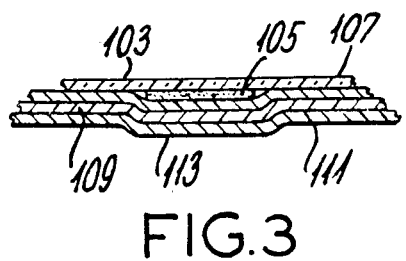
FIG.3
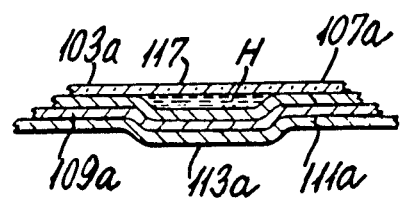
FIG.4

METHOD OF EARLY DETECTION OF BREAST CANCER

RELATED APPLICATION

This is a division of application Ser. No. 103,587, filed Dec. 14, 1979, now abandoned, which was a continuation-in-part of application Ser. No. 908,154, filed May 22, 1978, issued as U.S. Pat. No. 4,190,058 granted Feb. 26, 1980 and reissued Oct. 8, 1985 as U.S. Pat. No. Re. 32,000.

FIELD OF INVENTION

This invention relates to a method for the early detection of malignant mammary tumors and is particularly related to a method of visual detection of breast cancer using a cancer detection patch incorporated into the breast-receiving cups of a brassiere.

BACKGROUND OF INVENTION

Several techniques are currently employed for the detection of malignant tumors in the breast in order to determine if a woman's breast has been afflicted with cancer. As discussed in U.S. Pat. No. 3,847,139, issued on Nov. 12, 1974 to Eric Flam, thermography is, at the present, the technique which is most widely used in medical diagnostics for the detection of breast cancer. Other procedures include physical examination, mammography and xerography.

Physical examination involves probing for lumps or masses in the breast and may be carried out by a physician or the woman herself. The disadvantage of this procedure is that lumps which are large enough to be detected by probing or palpation have often spread far enough to other areas, thus reducing the efficacy of any treatment of the cancerous breast.

Both mammography and xerogrpahy involve X-ray examinations by an experienced technician or radiologist. The procedure is time consuming, expensive for the patient and often subjects the patient to repeated radiation dosages which could result in cumulative carcinogenic effects.

Thermography is based on infra-red scanning of the surface of the breast and developing a thermogram which contains temperature information corresponding to the scanned surface. Since the temperature of malignant mammary tissues are usually higher than the temperature of normal tissues, the thermogram affords a means by which the presence of localized hot spots can be detected. This technique, however, also involves the use of expensive equipment and expert technicians or radiologists to analyze and interpret the thermogram.

None of the aforementioned techniques lends itself to rapid or simple procedure for early detection of breast cancer and all of them require the patient to visit a physician, a hospital or a clinical center. Frequently, by the time the patient visits the physician or the hospital, the cancerous tissues have spread irreversibly and the chance of survival may have considerably diminished.

The aforementioned patent of Flam discloses a device which is intended to aid in early detection of breast cancer. The device disclosed by Flam comprises a structure including a substrate of stretchable, conformable material carrying a temperature responsive coating viewable against the background of the substrate. The temperature responsive coating is a liquid crystal system which reflects the components of incident light. When the device disclosed by Flam is worn by the woman as illustrated in FIG. 1 thereof, the temperature variations over the breast are transferred to the liquid crystal and a thermal pattern of color variations is developed which can be observed by a physician or the woman herself, and may be photographed. A single liquid crystal system with a wide temperature range, corresponding to the skin temperature of the breast of from about 85° F. to 95° F., is used as the temperature responsive coating, or a pair of liquid crystal systems can be used; one liquid crystal system covering the range of from about 85° F. to about 90° F., while the other liquid crystal system covers the range of from about 90° F. to about 95° F.

Another temperature-responsive device for detecting the presence of breast cancer is described by James et al in their U.S. Pat. No. 3,960,138, isssued on June 1, 1976. This device is retained in thermal contact with each breast by means of a brassiere, which also contains a differential temperature integrator circuit, whereby the difference in mean temperature between the two breasts may be integrated over a period of time.

A temperature-sensing patch is described in another patent (U.S. Pat. No. 3,661,142), granted to Erich Flam on May 9, 1972. The temperature-sensing patch disclosed in this patent comprises a flexible backing web having a pressure-sensitive adhesive coated on one side and a plurality of discrete temperature-sensitive indicators on the other side. Each indicator comprises a layer of encapsulated cholesteric liquid crystals, which contain cholesteric esters such as cholesteryl pelargonate (nonanate), cholesteryl chloride, oleyl cholesteryl carbonate, etc., which have the property of changing color with changes in temperature.

For further discussion of the various methods of detecting breast cancer see the article by Gershen-Cohen et al entitled "Modalities In Breast Cancer Detection Xerography, Mammography, Thermography, And Mammometry", in Cancer, December, 1969, pp. 1226-1230; see also "Advances In Thermography and Mammography", by Gershen-Cohen et al, Annals New York Academy of Sciences (1964), pp. 283-300 and "Relative Densiometric Analysis of Thermograms", by Brueschke et al., Annals New York Academy of Sciences (1964), pp. 82-89.

Notwithstanding the plethora of publications and diligent scientific research in breast cancer detection technology, xerography, mammography and thermography remain today as the principal methods which are available for the detection of breast cancer. As it was previously mentioned, however, all of these methods have inherent disadvantages and limitations and, in addition, they are not adapted for quick, initial mass screening which frequently proves to be a matter of life or death for persons at early stages of affliction with this disease.

In my copending application Ser. No. 908,154 filed May 22, 1978, now U.S. Pat. No. 4,190,058, granted Feb. 26, 1980, I have described a cancer detection patch for aid in early detection of breast cancer. The device disclosed in my aforesaid copending application is used by incorporating it into the breast-receiving cups of the brassiere, in contact with the breasts, and after few minutes, the device is visually examined and mirror image quadrants are compared to determine possible abnormality of the mammary tissues which warrants consultation with a physician and perhaps a more detailed examination to confirm presence or absence of cancer.

In order to obtain a more accurate indication of the breast temperature, I now provide the cancer detection patch described in my aforesaid application with a flexible conformable backing which when inserted into the breast-receiving cup of the brassiere, provides additional padding which insures a more intimate and conformable contact between the breast skin and the indicator surface of my cancer detection patch.

It is an object of this invention to provide a method for eary detection of breast cancer using a unique cancer detection patch, which method assures intimate contact between the breast skin and the temperature sensing surface of the patch for more accurate determination of possible abnormality in the mammary tissues.

The foregoing and other objects of this invention will be more clearly comprehended from the following detailed description of the invention and the accompanying drawings.

SUMMARY OF INVENTION

In accordance with this invention, a cancer detection patch and a method are provided for air in early detection of breast cancer. The patch, which is adapted for both home and institutional use comprises a heat-conductive web carrying on one surface an array of spaced-apart temperature indicators comprising a dye, or a pigment, and a temperature-sensitive substance having a relatively precise melting point approximately 0.5° F. different from the melting point of the temperature-sensitive substance in the adjacent indicator, wherein each of said indicators displays a change in color upon melting of the temperature-sensitive substance therein; a transparent layer overlying said heat-conductive web and sealed thereto; a backing web made of a flexible, compressible material secured to the other side of said heat-conductive web and a pealable layer adhesively secured to said backing web.

The method comprises placing a patch in each of the breast-receiving cups of the brassiere such that the temperature indicator-bearing surface of the patch is tightly pressed against the breast skin, in conformable, contiguous contact therewith. After several minutes (usually 5 to 15 minutes) the patches are removed and the temperature in mirror image quadrants of the breast are compared by visual observations of the temperature indicators of the respective quadrant patch.

A higher temperature in one breast may be indicative of existence of abnormality and possible cancer, requiring a followup complete examination by a physician.

BRIEF DESCRIPTION OF DRAWINGS

FIG. 1 is a plan view of the cancer detection patch used in the present invention;

FIG. 2 is a plan view of a quadrant of the cancer detection patch shown in FIG. 1;

FIG. 3 is a sectional view taken along the line 3—3 in FIG. 2;

FIG. 4 is a sectional view similar to FIG. 3 but illustrating a different embodiment of the invention; and FIG. 5 is a side view illustrating the use of the cancer detection patch and its backing web in the breast-receiving cup of a brassiere.

DETAILED DESCRIPTION OF INVENTION

It is well known that the average difference in surface temperature of the breasts is larger for persons with malignant tumors in one breast than those having normal (non-maligant) breasts. Moreover, the temperature difference in malignant mammary tumors is usually more than 1° C. (1.8° F.), and is invariably more than 0.6° C. (1.08° F.). Also, while the temperature of a normal breast tends to fluctuate, the temperature of a malignant breast remains relatively constant, and at a higher temperature than the temperature of the normal breast.

This invention is predicated upon the discovery that such differences in temperature between malignant and non-malignant breasts can be detected—and visually displayed—by means of a novel and unique device which is characterized by its simplicity and reliability for aiding in early detection of breast cancer. Simplicity of its use makes the device of this invention readily adaptable for mass screening and affords a rapid means whereby a person can determine if she (or he) is afflicted with breast cancer before undergoing a more comprehensive examination by a physician by means of xerography, thermography or mammography.

Referring now to the drawings wherein like reference numerals are employed to designate like parts, the device is shown in FIG. 1 in the form of a disc-shaped patch 101 comprising a flexible, conformabe heat-conductive material 103 which may conveniently and preferably be an aluminum foil having a thickness of from about 1 to about 3 mls. The disc-shaped patch 101 may be made in various convenient sizes ranging from about 5 inches to about 7 inches in diameter for insertion into the breast-receiving cups of a brassiere as will hereinafter be described. The patch 101 usually consists of four generally pie-shaped segments 101a, 101b, 101c and 101d which are essentially identical in sizes and configurations, and which, for convenience, will be referred to as quadrants, with each quadrant comprising an array of radially disposed, spaced apart indicators 105 in the form of strips, dots, etc. Eighteen indicators are shown in each quadrant, with each indicator adapted to display a visual change in color corresponding to a predetermined temperature.

In the embodiment illustrated in FIGS. 1 and 2, the indicators are identified by a plurality of adjacent indicia ranging from 1 to 18, corresponding to the temperature range of 89° to 97.5° F., in 0.5° F. gradations, as follows:

| Indicator No. | Corresponding Temperature, °F. |
| --- | --- |
| 1 | 89 |
| 2 | 89.5 |
| 3 | 90 |
| 4 | 90.5 |
| 5 | 91 |
| 6 | 91.5 |
| 7 | 92 |
| 8 | 92.5 |
| 9 | 93 |
| 10 | 93.5 |
| 11 | 94 |
| 12 | 94.5 |
| 13 | 95 |
| 14 | 95.5 |
| 15 | 96 |
| 16 | 96.5 |
| 17 | 97 |
| 18 | 97.5 |

The number of indicators as well as the temperature range and temperature gradations may vary, however, for breast cancer detection, and using the device illustrated in FIGS. 1 and 2, eighteen indicators per quadrant covering the aforementioned temperature range, in 0.5° F. gradations, are quite satisfactory.

The indicators 105 are formed as follows: Specially manufactured paper available from the National Cash Register, Dayton, Ohio, is precut into as many strips as are needed for each patch. For the embodiment illustrated in FIG. 1, eighteen such indicator strips are shown in each quadrant. The length and width of the indicator strips are not, per se, critical and usually, they are pecut to suitable dimensions so that eighteen such indicator strips may be spaced apart radially, in each quadrant of the patch.

The specially treated indicator paper which comprises a dye or a pigment, or any other indicator paper which may be treated with a suitable dye or pigment, is then treated (e.g., impregnated) with a thermally-responsive, temperature-sensitive substance which melts at a relatively precise temperature ranging from 89° F. to 97.5° F. A host of chemical compounds naturally suggest themselves for this application and are available from a variety of sources. It is important to note, however, that in the practice of this invention, each indicator strip comprises a substance or chemical which not only melts at one of the aforesaid temperature range, but its melting point must be approximately 0.5° F. different from the melting point of the chemical in the next indicator. Thus, the indicator strip corresponding to the numeral 1 comprises a chemical which melts at 89.0° F., the indicator corresponding to the numeral 2 comprises a chemical which melts at 89.5° F. and so on, until the indicator which is designated by the numeral 20 which comprises a substance which melts at 97.5° F.

The chemicals employed in the practice of this invention are preferably crystalline organic chemicals with relatively precise and sharp melting points at the aforementioned temperature range which do not recrystallize upon standing at ambient temperatures (room temperature).

The indicator strips 105, after treatment and impregnation with a dye or a pigment and a temperature-sensitive substance as aforesaid, are printed, embossed or otherwise suitably arrayed on the patch 101 as previously described and the patch is then covered with a flexible, transparent plastic layer 107 such as Mylar, nylon or Surlyn, etc., and heat sealed.

In order to insure intimate contact with the skin, and hence a more precise determination of the temperature of the breast, the patch 101 is adhesively secured to a backing web 109 made of suitable flexible plastic having a sufficient thickness to impart structural integrity to the patch. The backing web 109 is preferably made of a compressible plastic foam made of polyester, nylon fiber mesh, and the like, and is generally ½ to 1 inch thick and typically is ¾ inch thick. Accordingly, it constitutes an integral part of the cancer detection patch although it may be used separately in conjunction therewith to insure that the indicator-bearing surface of the patch is in intimate contact with the breast skin along its contours. Since the shapes and sizes of breasts vary considerably in different persons, the backing web insures that when the cancer detection patch is placed in the breast-receiving cup of a brassiere, there are no gaps or air pockets between the breast skin and the indicator-bearing surface of the patch which could interfere with accurate temperature determination.

Referring once again to FIG. 3, the underside of the backing web 109 is provided with an adhesive layer 111 for adhesively securing a pealable release layer 113.

In use, and as is shown in FIG. 5, the release paper 111 is first removed and the patch is inserted into each breast-receiving cup 115 of the brassiere such that adhesive layer 111 is secured to the inside surface of the cup 115 and the indicator-bearing surface 103 is in intimate, contiguous and conformable contact with the breast surface. Since the backing web 109 is a flexible, compressible material, intimate contact is assured between the indicator-bearing surface of the patch and the breast skin thereby assuring a reliable temperature determination. The use of the cancer detection patch in accordance with this invention permits mirror image sections of breast quadrants to be scanned. After a few minutes, the patch is removed from the brassiere and each patch is visually examined by comparing the number of indicator strips in mirror image quadrants which have displayed a change in color due to melting of the temperature sensitive chemicals used therein. The change in color is either from white to blue or vice-versa depending on the chemicals and dyes or pigments which are employed, although the exact color may be different for other chemicals-dyes or pigments combinations.

Since this test is relatively simple to perform and does not require any expertise or complicated equipment, it may be repeated two or three times to confirm the initial observations.

Numerous advantages become immediately apparent from the foregoing description of the invention. The test may be performed at home and as frequently as desired without visiting a physician or a clinical center.

While the invention has heretofore been described with a certain degree of particularity, naturally, some changes and modifications may be made therein which are nevertheless within the scope of this invention. For example, and instead of using chemically-impregnated indicator papers comprising a dye or a pigment, the chemical and the dye may be pre-mixed and then deposited as an array of spaced-apart radially disposed indicators much in the form of indicator strips 105 as shown in FIG. 1. The mixture of chemical and the dye (or pigment) is thus imprinted on the disc-shaped patch 101 such that a sectional view thereof is as illustrated in FIG. 4.

Referring now to FIG. 4, there is shown the aluminum foil 103a which may be slightly indented as in 117, shown in exaggerated dimensions. As in the embodiment shown in FIG. 3, the aluminum foil 103a is adhesively secured to a backing web 109a as in FIG. 3 and an undesired adhesive layer 111a for adhesively securing a pealable release layer 113a.

The temperature sensitive material H (a mixture of chemical and a dye or a pigment) is deposited in the indented area 117 and a transparent plastic layer 107a, e.g., Mylar, nylon, or Surlyn overlies the top surfaces of the aluminum foil and is heat sealed thereto.

In the embodiment shown in FIG. 3, when the disc-shaped patch is used to scan the surface of the breast as hereinbefore described, all chemicals melt at their respective melting points thus displaying a visible change in color. The number of indicators which have displayed a change in color are compared mirror image quadrants of the two breast as previously described in order to determine if there is any abnormality in the mammary tissues.

Also, while the device is shown in FIGS. 1 and 2 in the form of a disc-shaped member and a pie-shaped segment, respectively, these configurations may vary somewhat without changing the underlying inventive concept. Additionally, more or less than four quadrants or segments may be used to scan each breast so long as mirror image segments of the breasts are compared as aforesaid. However, and as a matter of convenience, the device shown in FIGS. 1 and 2 is more practical since it may be sized to conformably cover the breast area.

Other embodiments suggest themselves from the foregoing detailed description which are nevertheless within the scope and spirit of this invention.

What is claimed is:

1. A method of early detection of abnormalities in the body by comparison of the skin temperature of an area on one side of the body with that of a corresponding area on the other side, which comprises applying to the said areas two temperature sensors, each having temperature indicators which melt at predetermined temperatures to display a change in appearance, the indicators in each sensor being arranged in a pattern to form an array substantially covering the area of skin of temperature to be sensed, the patterns of the indicators of the arrays being comparable and the several indicators in one array having melting temperatures different from each other but identical with comparable indicators in the other array to facilitate temperature comparison of the two areas, and bringing the indicators into conforming contiguous contact with said area by pressing the indicators thereagainst by applying pressure thereto through a backing comprising a substantial thickness of a flexible compressible material.

2. A method of early detection of breast cancer by comparison of the skin temperature of an area of one breast with that of a corresponding mirror image area of the other breast, which comprises superimposing on each of the two areas a temperature sensor having temperature indicators which melt at predetermined temperatures to display a change in appearance, the indicators in each sensor being arranged in a pattern to form an array substantially covering the area of skin of temperature to be sensed, the patterns of the indicators of the arrays being comparable and the several indicators in one array having melting temperatures different from each other but identical with comparable indicators in the mirror image array of the other sensor to facilitate temperature comparison of the two areas, and bringing the indicators into conforming contiguous contact with said areas by pressing the indicators thereagainst by applying pressure thereto through a backing comprising a substantial thickness of a flexible compressible material.

* * * * *

UNITED STATES PATENT AND TRADEMARK OFFICE
CERTIFICATE OF CORRECTION

PATENT NO. : 4,624,264

DATED : November 25, 1986

INVENTOR(S) : ZSIGMOND L. SAGI

It is certified that error appears in the above—identified patent and that said Letters Patent is hereby corrected as shown below:

Column 3, line 24, "air" should be--aid--.

Column 4, line 25, "conformabe" should be--conformable--.

Column 6, line 53, "undesired" should be--underside--.

Signed and Sealed this

First Day of March, 1988

Attest:

DONALD J. QUIGG

Attesting Officer

Commissioner of Patents and Trademarks